(12) United States Patent
Beger

(10) Patent No.: US 6,639,789 B2
(45) Date of Patent: Oct. 28, 2003

(54) INSTRUMENT AND SERVICE UNIT FOR A SURGICAL OPERATING AREA

(75) Inventor: Frank Beger, Cologne (DE)

(73) Assignee: Karl Storz GmbH & Co. KG (DE)

( * ) Notice: Subject to any disclaimer, the term of this patent is extended or adjusted under 35 U.S.C. 154(b) by 14 days.

(21) Appl. No.: 10/090,708

(22) Filed: Mar. 5, 2002

(65) Prior Publication Data

US 2002/0080571 A1 Jun. 27, 2002

Related U.S. Application Data

(63) Continuation-in-part of application No. 09/614,272, filed on Jul. 12, 2000.

(51) Int. Cl.[7] .............................. H05K 5/02; H05K 7/16; A61B 1/04; A61B 1/045
(52) U.S. Cl. ................... 361/681; 361/682; 361/683; 361/686; 606/46; 248/276.1; 74/490.01
(58) Field of Search .................................. 361/681–683, 361/686, 724–727; 128/906, 915, 916, 920; 606/1, 46; 248/317, 276.1; 74/490.01, 490.02, 490.03, 490.04, 490.05

(56) References Cited

U.S. PATENT DOCUMENTS

| | | | |
|---|---|---|---|
| 3,164,355 A | * | 1/1965 | Sietz et al. ............... 248/324 |
| 3,550,892 A | * | 12/1970 | Propst .................... 248/282.1 |
| 4,490,022 A | | 12/1984 | Reynolds |
| 4,625,731 A | | 12/1986 | Quedans et al. |
| 4,673,154 A | * | 6/1987 | Karapita .................. 248/320 |
| 4,705,048 A | | 11/1987 | Pfohl |
| 4,878,746 A | | 11/1989 | Nakano |
| 4,881,709 A | * | 11/1989 | Nakamura ............ 248/281.11 |
| 4,981,139 A | | 1/1991 | Pfohl |
| 4,987,488 A | | 1/1991 | Berei |
| 4,989,253 A | | 1/1991 | Liang et al. |
| 5,048,941 A | | 9/1991 | Hamada et al. |
| 5,077,769 A | | 12/1991 | Franciose |
| 5,129,397 A | | 7/1992 | Jingu et al. |
| 5,184,601 A | | 2/1993 | Putman |
| 5,251,611 A | | 10/1993 | Zehel et al. |
| 5,257,998 A | * | 11/1993 | Ota et al. .................. 606/130 |
| 5,359,417 A | | 10/1994 | Mueller et al. |
| 5,377,371 A | | 1/1995 | Foster |
| 5,431,645 A | | 7/1995 | Smith et al. |

(List continued on next page.)

FOREIGN PATENT DOCUMENTS

| | | | |
|---|---|---|---|
| DE | G9218373 | 12/1992 | |
| DE | 4307589 A1 | * 9/1993 | ........... A61B/19/00 |
| DE | 19714984 | 11/1997 | |

OTHER PUBLICATIONS

M. O. Schurr, et al. The Operating room system for endoscopic surgery: project OREST 1995 6 pages.

(List continued on next page.)

Primary Examiner—Anatoly Vortman
(74) Attorney, Agent, or Firm—St. Onge Steward Johnston & Reens LLC

(57) ABSTRACT

A centralized surgical instrument unit for use in a surgical operating area is provided. The surgical instrument unit includes a tripod having at least two articulating arms, one of which extends into a sterile operating area and another of which extends outside of the sterile operating area. A housing containing at least two instruments or instrument components is mounted to the articulating arm which extends outside of the sterile operating area. A user interface unit is mounted on the arm which extends into the sterile operating area. The user interface unit includes a central instrument status display unit and a central input unit, and displays instrument parameters and status to, and receives instrument commands from, personnel within the sterile operating area.

15 Claims, 4 Drawing Sheets

U.S. PATENT DOCUMENTS

| | | | |
|---|---|---|---|
| 5,733,263 A | | 3/1998 | Wheatman |
| 5,765,565 A | | 6/1998 | Adair |
| 5,805,335 A | | 9/1998 | Fukaya et al. |
| 5,820,623 A | * | 10/1998 | Ng ................................ 606/1 |
| 5,867,210 A | | 2/1999 | Rod |
| 5,873,814 A | | 2/1999 | Adair |
| 6,045,596 A | | 4/2000 | Holland et al. |
| 6,203,590 B1 | | 3/2001 | Byrd et al. |
| 6,213,481 B1 | * | 4/2001 | Marchese et al. ............. 280/35 |
| 6,434,329 B1 | * | 8/2002 | Dube et al. ................... 396/14 |
| 2001/0034530 A1 | * | 10/2001 | Malackowski et al. ..... 606/130 |

OTHER PUBLICATIONS

Siemens Information on the Integrated OR System 2 pages.

Dorier Deutsche Aerospace Dornier Orest. Minimal invasiver chirurgischer Arbeitsplatz.

Dornier Orest. Der erste Systemarbeitsplatz fur die minimal–invasive Chirurgie.

Dornier Orest. Systemarbeitsplatz fur die endoscopic chirurgie.

Comments of Frank Beger.

* cited by examiner

INSTRUMENT AND SERVICE UNIT FOR A SURGICAL OPERATING AREA

RELATED APPLICATIONS

This patent application is a continuation-in-part of currently pending U.S. patent application Ser. No. 09/614,272, filed Jul. 12, 2000.

FIELD OF THE INVENTION

The subject of the invention is an instrument and service unit for a surgical operating area.

BACKGROUND OF THE INVENTION

The system work station for endoscopic surgery set forth in DE 92 18 373 foresees a movable instrument cabinet to hold the utensils required for an operation, in which cabinet the instruments are stored as insertable tools and which, in a further elaboration of the invention, can be mounted on a ceiling console. In the sterile area, a swivel arm with a supply cable is erected to hold the instrument power lines. The swivel arm also holds a display unit and a service area for the apparatuses of the instrument cabinet.

An operating system made by the Siemens AG firm has also become known, which is designated as an SIOS system and which is constructed on the assembly-module principle and includes an instrument wagon, a suspended instrument service unit with connected appliance units such as scalpel, endoscope, and the like, and a monitor unit hung from the ceiling. This structure is intended to allow the operator to designate the instrument of his or her choosing, that is, a range of different instruments are built in to the system.

Invention DE 197 14 984 C2 introduced an integrated instrument and service unit for a surgical operating area, which includes a common housing, at least two instruments and/or appliance components, which are stored in the housing, a central control unit that is contained in the housing and directs and monitors the instrument functions, along with a central supply unit with central provision cables provided on the housing for input or output of data and/or operating media and a central display unit. In the following description, the term "supply" is to be understood as meaning the supply of the instrument and working unit as a whole. The term "provision" shall designate the supply on the patient's side.

The compact format allows the entire unit to be installed and centrally placed in the actual operating area, that is, at the level of the working space, so that by exploiting the unit's extremely reduced space requirement one can select an arrangement using a tripod, preferably a ceiling tripod. The display unit and the service unit can be movably mounted on the unit. Thus they can be separately situated in the optimal alignment for the operator, without the necessity of displacing the entire unit. The operating staff will have a great deal of working and moving space, with favorable viewing conditions and access to the individual components and servicing devices. Monitoring of the appliance is simple, and it can be operated practically within immediate reach.

With this integrated instrument and service unit, the instruments and instrument components that are integrated in the housing with their entire range of functions are centrally accessible, as is required for endoscopic surgery, and have central direction and monitoring available. Provision cables and tubes are directed through a central connecting area. The instruments are connected with the central control unit, that is, with the computer, at the interface points and they can be networked with one another.

Thanks to the centralized arrangement of the instruments and monitoring units, there can be a unified, easily visible user area, which allows important service parameters to be displayed directly and in combination for several instruments. In addition, several persons can view the central instrument status display unit at once. As a result, and through the greater visibility of the integrated construction, there are few instances of optical and acoustical communication errors. The instrument status display unit can still be read well even under relatively poor lighting conditions. The integrated model, moreover, helps ensure good hygienic conditions.

SUMMARY OF THE INVENTION

An object of the present invention is to create an instrument and service unit for a surgical operating area, which consists of an integrated instrument and service unit that can be moved into the working area, which unit allows for the use of a separate computer and instrument status display unit.

The instrument and service unit for a surgical operating area, according to one embodiment of the invention, consists of a tripod, in particular a ceiling tripod, a housing mounted on one arm of the tripod, at least two instruments and/or instrument components, which are installed in the housing, a central control unit which directs and monitors the instrument functions, a central service unit, a central supply unit with central provision connections on the housing for input and/or output of data and/or working media, and a central instrument status display unit. The central control unit, service unit, and instrument status display unit are combined as a single unit and movably connected with the integrated instrument and supply unit.

It is an advantage of the apparatus's design, that, on the one hand, an integrated arrangement of the instrument and supply unit is provided in the form of a single appliance, which fulfills the function of the customary individual instruments, so that a great deal of space is saved and the instrument and service unit can be handled ergonomically. At the same time, through the unified combination of control unit, service unit, and instrument status display unit, it is possible to achieve the linking of service and instrument status display units with the control unit, resulting in cost savings and technical advantages. In particular, a standard computer can be used, which proceeds to control the instruments by way of a data bus, so that only the instruments contained in the instrument housing require a separate control card (SCB card).

As a result of the separate arrangement of the control, service, and instrument status display unit, this unit can be simply and quickly replaced as a whole in the event of a defect or a system expansion, without requiring disassembly. The safety and flexibility of the instrument and service unit of this invention are further increased at the same time by good service qualities. In addition, the modular construction ensures that the technology can grow along with the increasing demands and applications. Also, the control, service, and instrument status display unit, for instance, can also serve as writing and organizing area at the operating table, if the need arises.

In a demonstration of the invention's instrument and service unit, the control, service, and instrument status display unit is mounted movably on the housing of the instrument and supply unit, or alternatively on its suspension attachment.

In another model, the unit made up of the control, service, and display unit can be installed on another arm of the tripod. This results in a still greater flexibility of the instrument status display and service for the operator and staff, depending on the reach of the pivot's arm.

It is particularly advantageous to use a touch screen.

In addition, remote control and/or voice control can be arranged.

An additional central control instrument status display provided on the housing of the instrument and supply unit, which indicates the instrument's specific values, ensures a clear reading by the entire operating team and contributes to quicker recognition of dangerous situations.

It is also advantageous to provide, on the housing of the instrument and supply unit, network switching controls, mechanical operating elements, or else, for instance, a focusing ring.

In another embodiment in which the tripod includes two articulating arms, one of the articulating arms extends into the sterile operating area, while the other arm extends outside of the sterile operating area. Mounted on the arm which extends into the sterile operating area is the central instrument status display unit and the central input unit for receiving instrument commands from personnel within the sterile operating area. Mounted on the arm which extends outside the sterile operating area is the housing which contains at least two instruments or instrument components.

The central instrument status display unit and the central input unit may preferably be integrated as a single touch-screen. A central control unit may be provided, and may be located in an area remote from the two articulating arms, such as in a ceiling tripod. One or more image display units may be provided for displaying images captured by an endoscope or the like. The image display units may be located on one of the articulating arms and/or in an area remote from the articulating arms.

BRIEF DESCRIPTION OF THE DRAWINGS

The invention is further described below by means of advantageous demonstration models and illustrations. This depiction serves merely for explanatory purposes and therefore should not be interpreted in ways that restrict the invention. The illustrations are as follows.

DETAILED DESCRIPTION OF AN EMBODIMENT OF THE INVENTION

Figure 3:
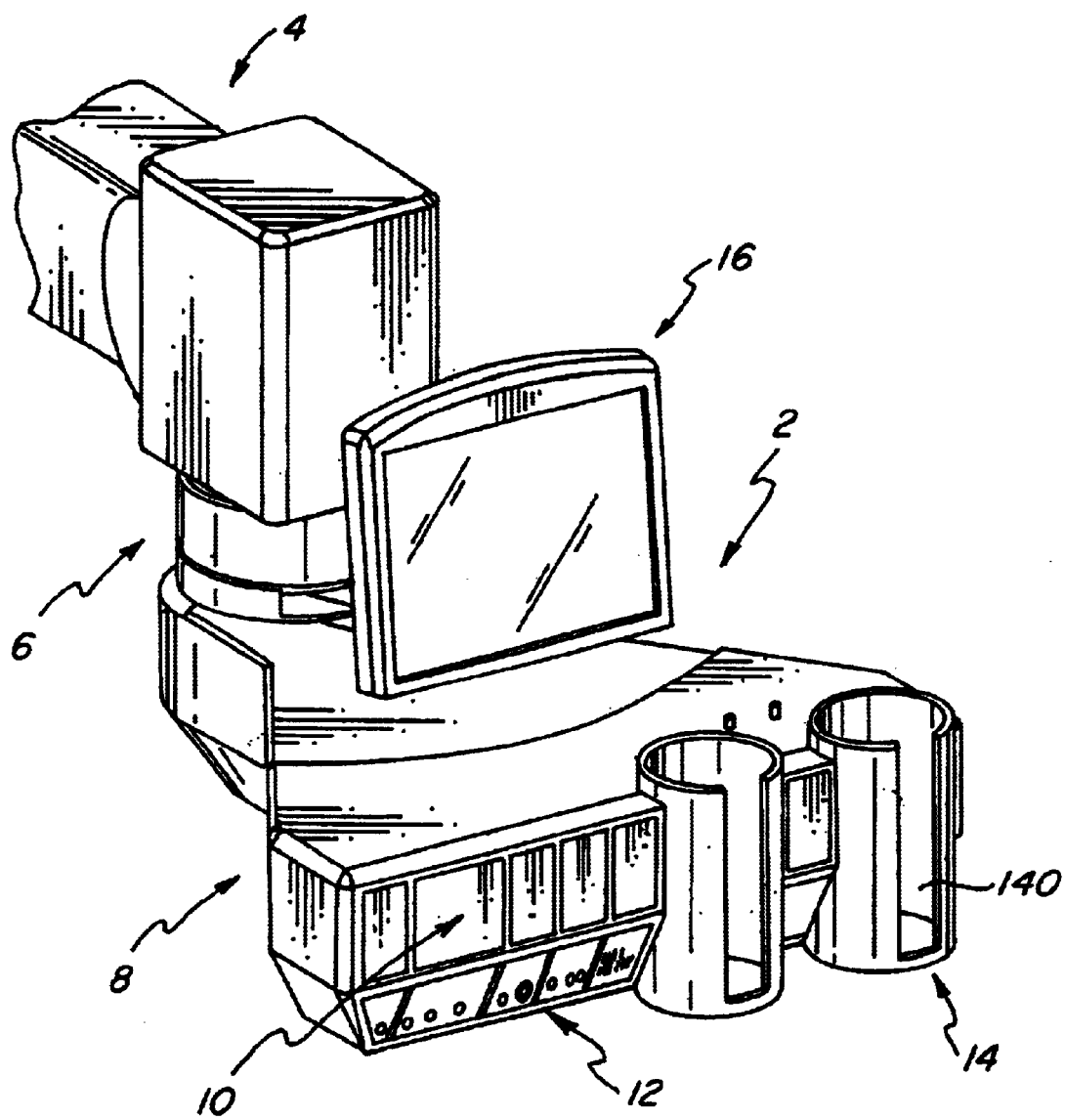
FIG. 3 is an isometric view of an integrated instrument and service unit according to the prior art.

Below we first describe a well-known integrated instrument and service unit according to invention DE 197 14 984 C2 as seen in FIG. 3.

This instrument and service unit 2 is mounted on or in a ceiling tripod 4 by means of a mounting 6 that rotates. It includes a housing 8, in which all important instruments and instrument components are integrated. Toward the front of the housing 89 are a central control unit 10, a central connection field or connecting terminal 12 with provision connections and bottle holders 14 for rinsing and feeding bottles. On the housing there is a service monitor 16 with touch screen, which can be swung, rotated, and tilted.

The bottle holders 14 have slits or open areas on the front side, which serve as windows. In this way one can simply check visibly to see the liquid level in the bottles contained there (rinsing and feeding bottles). Varying levels of liquid content can allow, for instance, a patient's loss of blood to be clearly determined, a matter of some importance for the operation and post-operative therapy. On the upper side of the housing 8, directly behind the bottle holders 14, there are two connector points for connector hoses for the bottles. In the illustrated model, one of the two bottle holders 14, in this case the one provided for liquid rinsing on the left, is heatable, so that the rinsing liquid can be heated up to 42.5 degrees C.

Below, the arrangement of the instrument and service unit, according to this invention, is explained by means of three demonstration models shown in FIGS. 1, 2A and 2B. Since a number of parts are the same as those of the instrument and service unit of FIG. 3, they are designated with the same numerals and will not be described again. To simplify the illustration, units of the housing 8, its supply cables, and the like, are omitted.

Thus we see once again a ceiling tripod 4 with a suspension cable 6. The ceiling tripod has several arm segments, 410, 420, 430, which are steered by means of turnable joints 412, 422, and 432. An additional turnable joint 434 provides a rotating connection for the housing 8, so that the turnable joints and arm segments together make up one tripod arm and thus the suspension 6 for the housing 8. The housing 8, as in the customary unit, contains the instruments or instrument components as well as the supply unit with the provision connections. The supply lines lead through the suspension 6. These parts, as mentioned, will not be further described.

Arm segment 430 is equipped with a mounting 1602, on which a swivel arm 1604 is connected to a mounting framework 1608 that can rotate around a vertical axis 1606. The mounting framework 1608 carries a swiveling unit 1600, that contains the control unit, service unit, and instrument status display unit. The control unit in the illustrated model is a commercially available computer, and the service and display unit is a touch screen. The electrical lines run through the container parts, as seen at 1610.

Figure 1:
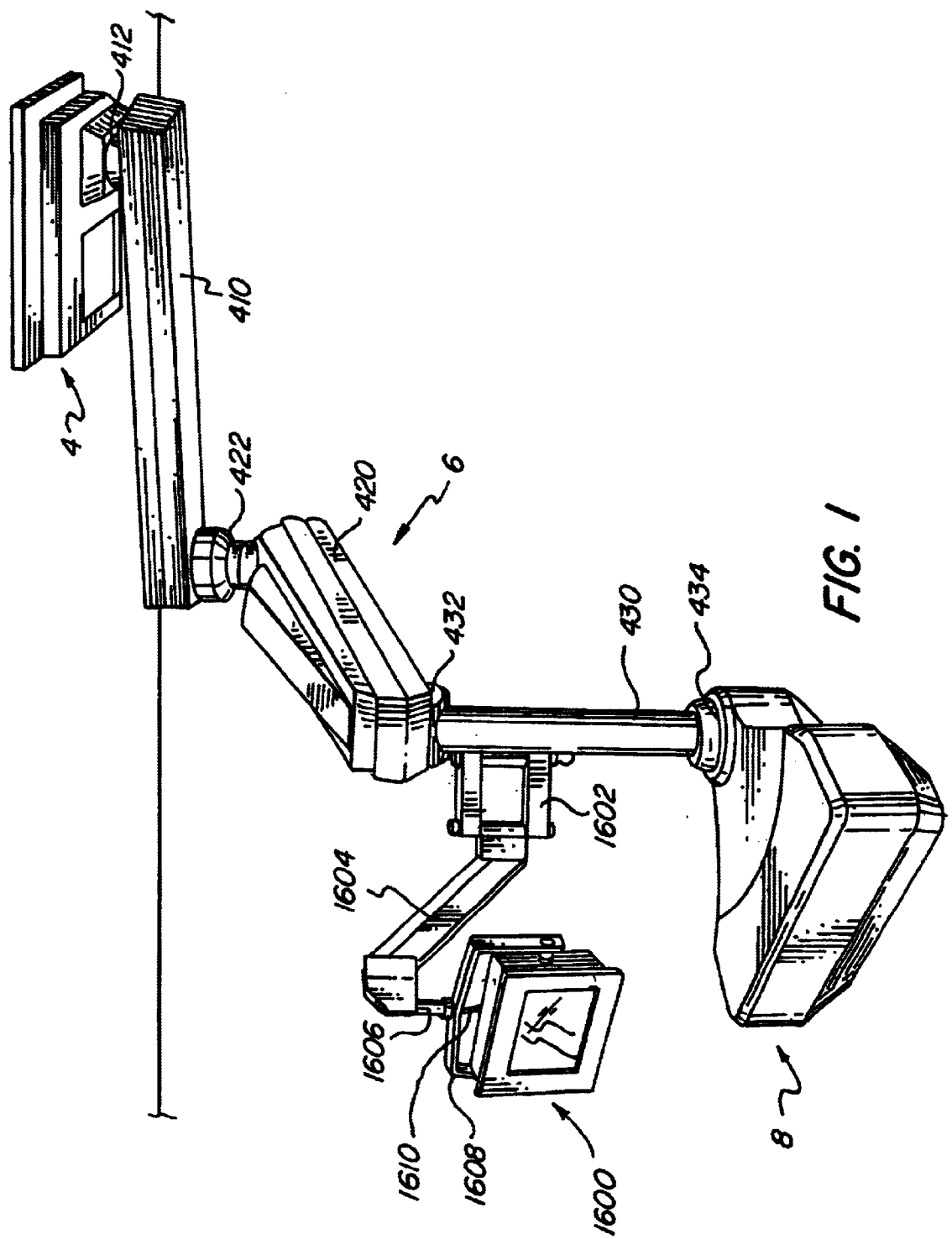
FIG. 1 is an isometric view of an instrument and service unit according to a first illustrative model, mounted on a ceiling tripod.
Figure 2A:
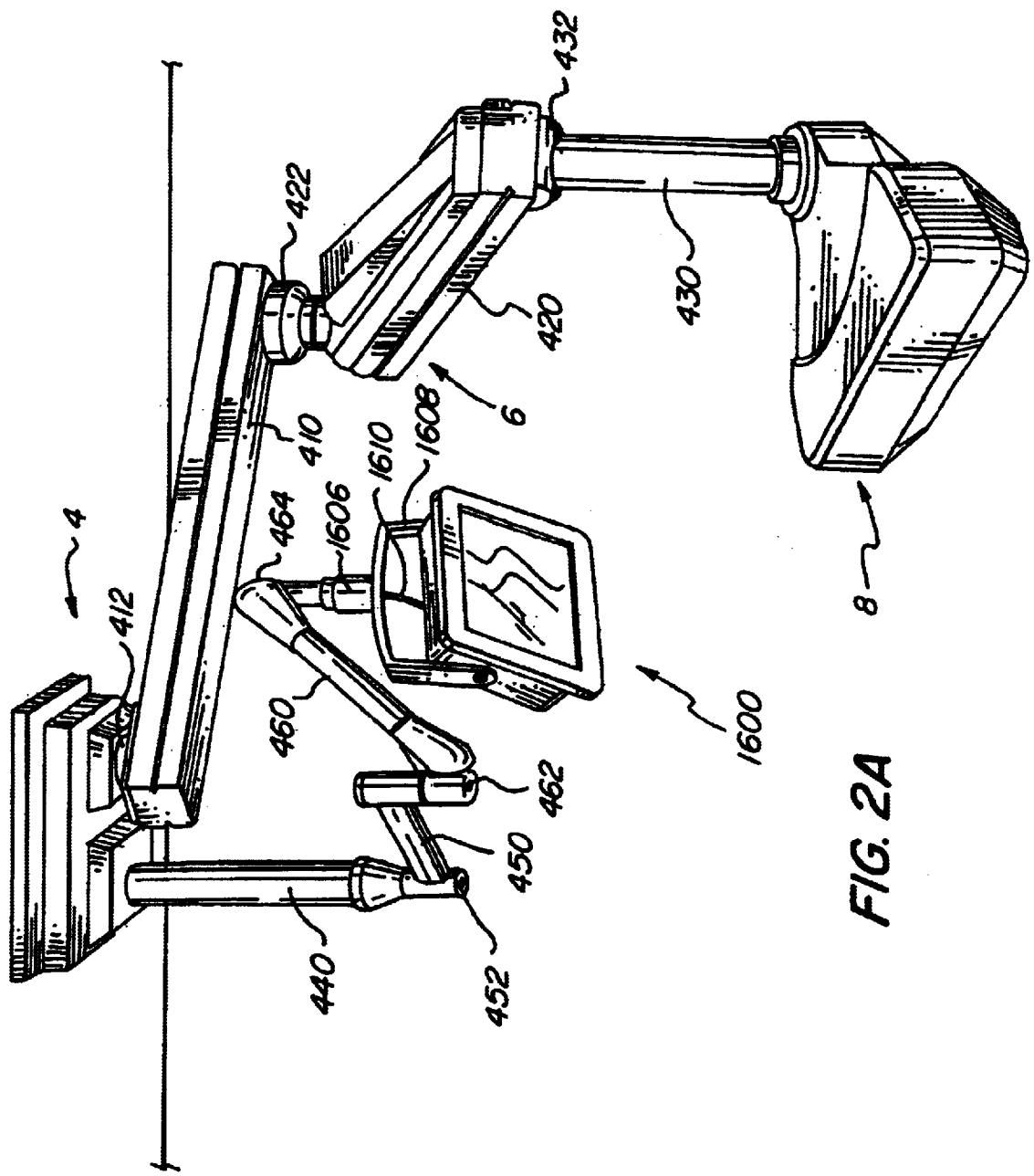
FIG. 2A is an isometric view of an instrument and service unit according to a second illustrative model.

In the second model of the invention, shown in FIG. 2A, the housing 8 is mounted as in the first model, so that it is sufficient in this respect to refer the reader to FIG. 1.

The user interface unit 1600, thus, is not movably mounted on the suspension of the housing 8, but rather like the housing is connected to tripod 4. The ceiling tripod 4 accordingly has additional arm segments 440, 450, and 460, which are connected by means of the turnable joint 452 and pivot joints 462, 464. The container framework 1608 of user interface unit 1600 can be turned along the vertical axis 1608. Electric connections 1610 go by way of the suspension cable 440 to 1606 of user interface unit 1600, that is, the second tripod arm.

Figure 2B:
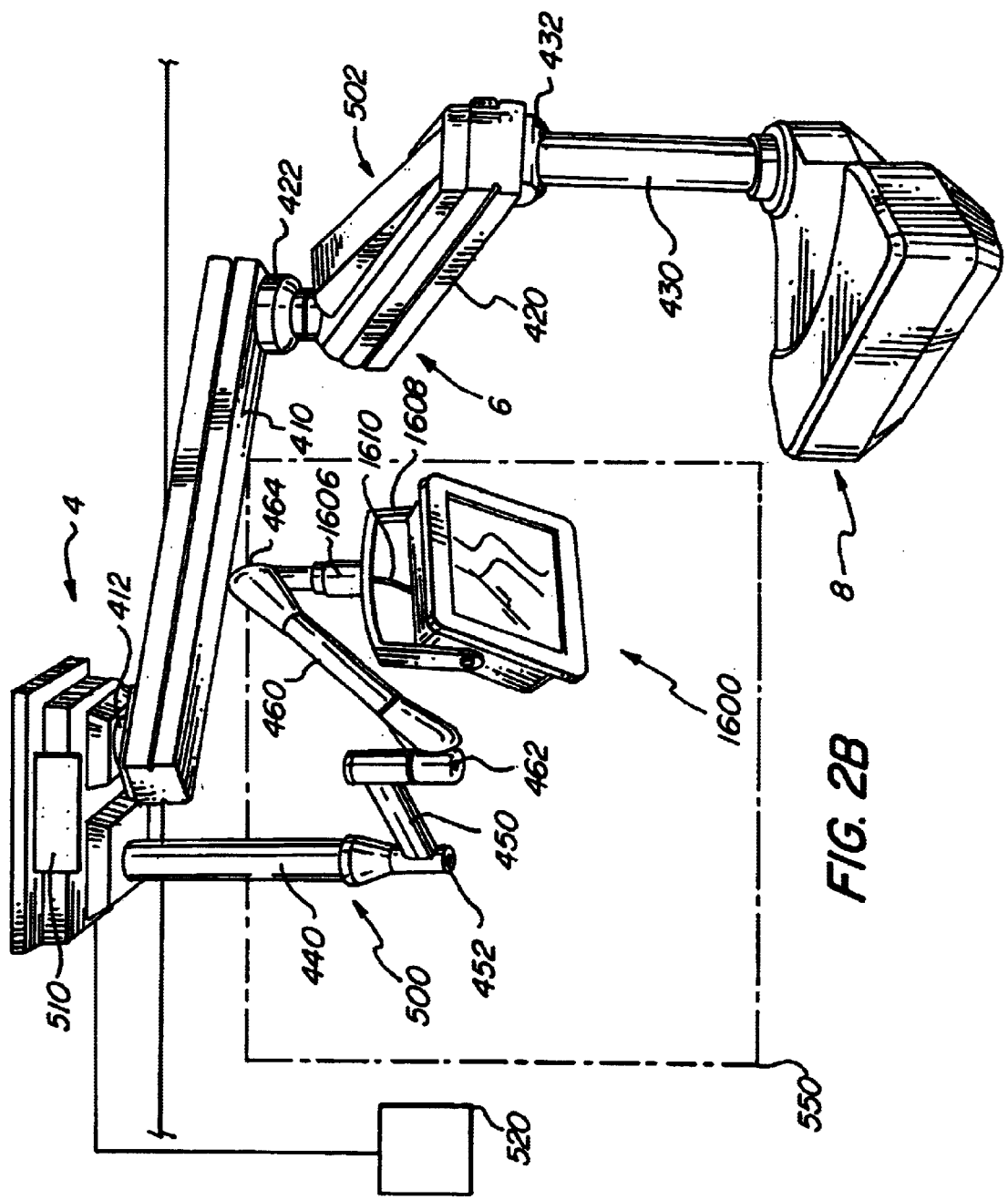
FIG. 2B is an isometric view of an instrument and service unit according to a third illustrative model.

In the third model of the invention, shown in FIG. 2B, the tripod 4 includes two articulating arms, one of the articulating arms 500 extending into the sterile operating area 550, while the other arm 502 extends outside of the sterile operating area 550. The housing 8 which contains at least two instruments or instrument components is mounted as in the first model to the arm 502 which extends outside of the sterile operating area 550, so that it is sufficient in this respect to refer the reader to FIGS. 1 and 2A.

Mounted on the arm 500 which extends into the sterile operating area 550 is the user interface unit 1600 that contains the instrument status display unit and the central input unit for receiving instrument commands from personnel within the sterile operating area 550. Unit 1600 is preferably a touchscreen which integrates the central instrument status display unit and the central input unit. A central control unit 510 may be provided for controlling operation of the centralized surgical instrument control unit, and may be located in an area remote from the two articulating arms, such as in a ceiling tripod 4. One or more image display 520 units, such as televisions, computer monitors, video projectors or the like, may be provided for displaying images captured by an endoscope or the like. The image display units 520 may be located on one of the articulating arms and/or in an area remote from the articulating arms. If desired, the image display unit may be integrated into user interface unit 1600.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A centralized surgical instrument unit for use in a surgical operating area, comprising:
    a tripod having at least two articulating arms, one of the arms extending into a sterile operating area and another of the arms extending outside of the sterile operating area;
    a housing mounted to the articulating arm which extends outside of the sterile operating area, said housing containing at least two instruments or instrument components; and
    a user interface unit mounted on the arm which extends into the sterile operating area, said user interface unit including a central instrument status display unit and a central input unit, said user interface unit displaying instrument parameters and status to, and receiving instrument commands from, personnel within the sterile operating area.

2. The centralized surgical instrument unit of claim 1 wherein said user interface unit comprises a touchscreen which integrates the central instrument status display unit and the central input unit.

3. The centralized surgical instrument unit of claim 1 further comprising a central control unit for controlling operation of the centralized surgical instrument control unit.

4. The centralized surgical instrument unit of claim 3 wherein said central control unit is located in an area remote from the articulating arms.

5. The centralized surgical instrument unit of claim 4 wherein said central control unit is located in said tripod.

6. The centralized surgical instrument unit of claim 1 further comprising at least one image display unit for displaying images captured by an endoscope.

7. The centralized surgical instrument unit of claim 6 wherein said at least one image display unit is located in an area remote from the articulating arms.

8. The centralized surgical instrument unit of claim 6 wherein said at least one image display unit is located on one of the articulating arms.

9. The centralized surgical instrument unit of claim 8 wherein said at least one image display unit is integrated into said user interface unit.

10. A centralized surgical instrument unit for use in a surgical operating area, comprising:
    a tripod having at least two articulating arms, one of the arms extending into a sterile operating area and another of the arms extending outside of the sterile operating area;
    a housing mounted to the articulating arm which extends outside of the sterile operating area, said housing containing at least two instruments or instrument components;
    a touchscreen mounted on the arm which extends into the sterile operating area, said touchscreen including a central instrument status display unit and a central input unit, said touchscreen displaying instrument parameters and status to, and receiving instrument commands from, personnel within the sterile operating area;
    a central control unit for controlling operation of the centralized surgical instrument control unit; and
    at least one image display unit for displaying images captured by an endoscope.

11. The centralized surgical instrument unit of claim 10 wherein said central control unit is located in an area remote from the articulating arms.

12. The centralized surgical instrument unit of claim 10 wherein said central control unit is located in said tripod.

13. The centralized surgical instrument unit of claim 10 wherein said at least one image display unit is located in an area remote from the articulating arms.

14. The centralized surgical instrument unit of claim 10 wherein said at least one image display unit is located on one of the articulating arms.

15. The centralized surgical instrument unit of claim 14 wherein said at least one image display unit is integrated into said touchscreen.

* * * * *